(12) United States Patent
Rabinovich-Guilatti et al.

(10) Patent No.: US 7,973,081 B2
(45) Date of Patent: *Jul. 5, 2011

(54) EMULSION COMPOSITIONS CONTAINING QUATERNARY AMMONIUM COMPOUNDS

(75) Inventors: Laura Rabinovich-Guilatti, Kadima (IL); Gregory Lambert, Chatenay Malabry (FR); Frederic Lallemand, Fresnes (FR); Betty Philips, Antony (FR)

(73) Assignee: Novagali Pharma SA, Evry (FR)

( * ) Notice: Subject to any disclaimer, the term of this patent is extended or adjusted under 35 U.S.C. 154(b) by 262 days.

This patent is subject to a terminal disclaimer.

(21) Appl. No.: 11/829,428

(22) Filed: Jul. 27, 2007

(65) Prior Publication Data

US 2008/0026991 A1    Jan. 31, 2008

Related U.S. Application Data

(63) Continuation-in-part of application No. 11/494,493, filed on Jul. 28, 2006, now abandoned.

(30) Foreign Application Priority Data

Jul. 28, 2006  (EP) ..................................... 06291236
Jul. 9, 2007   (EP) ..................................... 07112097
Jul. 10, 2007  (WO) .................. PCT/IB2007/053441

(51) Int. Cl.
| | |
|---|---|
| *A61K 9/107* | (2006.01) |
| *A61K 9/00* | (2006.01) |
| *A61K 47/30* | (2006.01) |
| *A61K 38/00* | (2006.01) |
| *A61K 38/12* | (2006.01) |
| *A61K 38/13* | (2006.01) |
| *A01N 33/12* | (2006.01) |
| *A01N 25/04* | (2006.01) |
| *A01N 25/30* | (2006.01) |

(52) U.S. Cl. ................ 514/643; 514/642; 514/2; 514/9; 514/11; 514/15; 514/772.3; 514/785; 514/786; 424/78.04; 424/400; 424/427

(58) Field of Classification Search ........................ None
See application file for complete search history.

(56) References Cited

U.S. PATENT DOCUMENTS 3,954,644 A    5/1976  Krezanoski et al.
(Continued)

FOREIGN PATENT DOCUMENTS

EP        0642782        3/1995
(Continued)

OTHER PUBLICATIONS

Household Products Database entry for Mineral Oil accessed Jul. 7, 2010 at http://householdproducts.nlm.nih.gov/cgi-bin/household/brands?tbl=chem&id=227.*

(Continued)

*Primary Examiner* — Sharmila Gollamudi Landau
*Assistant Examiner* — Kevin S Orwig
(74) *Attorney, Agent, or Firm* — Young & Thompson

(57) ABSTRACT

Composition containing quaternary ammonium compounds in which the nitrogen atom is substituted by at least one alkyl group having at least 12 carbon atoms, the composition including at least 20% in weight by weight of the total composition, of ammonium halides in which the nitrogen atom is substituted by at least one alkyl group having at least 14 carbon atoms and more than 5%, preferably more than 7% in weight by weight of the total composition, of ammonium halides in which the nitrogen atom is substituted by at least one alkyl group having at least 16 carbon atoms. Ophthalmic oil-in-water emulsions containing such compositions, the ophthalmic emulsions being useful for eye care or for the treatment of eye conditions are also disclosed.

9 Claims, 2 Drawing Sheets

U.S. PATENT DOCUMENTS

Figure 1:
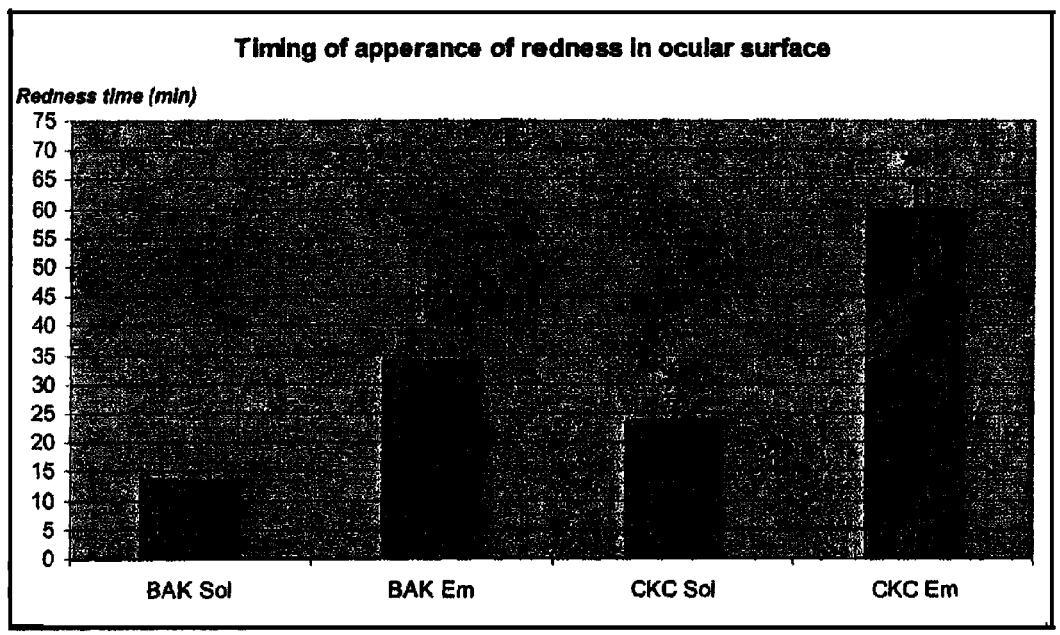

| | | | |
|---|---|---|---|
| 5,190,936 A | 3/1993 | Laugier et al. | |
| 5,951,988 A | 9/1999 | Littel-van den Hurk et al. | |
| 6,375,936 B1* | 4/2002 | Allard et al. | 424/59 |
| 6,656,460 B2* | 12/2003 | Benita et al. | 424/78.04 |
| 2002/0169138 A1* | 11/2002 | Kunz et al. | 514/44 |
| 2005/0059644 A1* | 3/2005 | Rood et al. | 514/171 |
| 2006/0100288 A1* | 5/2006 | Bague et al. | 514/642 |
| 2007/0248645 A1* | 10/2007 | Bague et al. | 424/427 |
| 2008/0025941 A1 | 1/2008 | Rabinovich-Guilatt et al. | |
| 2008/0107738 A1* | 5/2008 | Philips et al. | 424/489 |
| 2008/0268020 A1* | 10/2008 | Philips et al. | 424/427 |
| 2009/0018057 A1* | 1/2009 | Lambert et al. | 514/11 |

FOREIGN PATENT DOCUMENTS

| | | |
|---|---|---|
| EP | 1655021 | 5/2006 |
| GB | 633175 | 12/1949 |
| WO | WO9531958 | 11/1995 |
| WO | WO9725975 | 7/1997 |
| WO | WO9825620 | 6/1998 |
| WO | WO0122936 | 4/2001 |
| WO | WO2006050836 | 5/2006 |

OTHER PUBLICATIONS

European Search Report May 2, 2007.

International Search Report Apr. 2, 2008.

Robiot, Cetalkonium Chloride Product Info., Copyright 2003, p. 1.

Generic Name: Latanoprost, MedicineNet.com, Jul. 23, 1998, pp. 1-2.

* cited by examiner

EMULSION COMPOSITIONS CONTAINING QUATERNARY AMMONIUM COMPOUNDS

This invention relates to pharmaceutical, ophthalmic or cosmetic compositions containing quaternary ammonium compounds, more preferably to ophthalmic emulsions being useful for eye care or for the treatment of eye conditions. This invention also relates to compositions including at least one quaternary ammonium compound as cationic agent.

Quaternary ammonium compounds are organic compounds usually used as an antiseptic or antimicrobial agent. For example, benzalkonium chloride is a nitrogenous cationic surface-acting agent belonging to the quaternary ammonium group. Benzalkonium chloride is generally defined as a mixtures of compounds of general formula $C_6H_5CH_2N(CH_3)_2RCl$, wherein R is a C12-C24 alkyl group.

Benzalkonium chloride, as usually provided by the manufacturers wanting to comply with the European and/or American Pharmacopeia, is a mixture of n-alkyl dimethyl benzyl ammonium chlorides of various alkyl chain lengths. For example, FeF Chemicals A/S (Denmark) supplies, under reference 8100301U (BAK USP/NF), a mixture of three alkyl dimethyl benzyl ammonium chlorides including: (1) 60-70% of $C_{12}$-alkyl dimethyl benzyl ammonium chloride (2) 30-40% of $C_{14}$-alkyl dimethyl benzyl ammonium chloride, and less than 5% of $C_{16}$-alkyl dimethyl benzyl ammonium chloride.

Benzalkonium chloride, as a mixture of alkyl dimethyl benzyl ammonium having various alkyl chain lengths is used as preservative agent in topical ophthalmic products. Benzalkonium chloride also has cationic agent properties, and was used as cationic agents for emulsions, especially ophthalmic emulsions.

When mixtures of benzalkonium chlorides having various alkyl chain lengths are used in emulsions, they may act both as preservative agents and cationic agents.

The Applicant worked on long chain quaternary ammonium compounds, and noticed that the length of the alkyl chain was important with regards to the function performed by the quaternary ammonium compounds: acting on the length of the alkyl chain resulted in enhancing or reducing the cationic power of the quaternary ammonium compounds. Without wanting to be linked by any theory, the Applicant observed on working on oil-in-water emulsions, that long chain quaternary ammonium compounds are preferentially localized at the oil/water interface of the emulsions, resulting in (1) emulsions with higher zeta potential and (2) more stable emulsions. As quaternary ammonium may be considered as undesirable or toxic, it is thus a goal of this invention to provide cationic composition having a reduced content of quaternary ammonium compound.

The Applicant also observed that, in emulsions, quaternary ammonium compounds having long alkyl chains, for example quaternary ammonium compounds having C14-C18 alkyl chains, when compared to C12-alkyl chains, did not have a good bactericidal activity, whereas they conferred a greatest cationic power.

Moreover, the Applicant observed that long chain quaternary ammonium compounds were present preferentially at the oil/water interface of the emulsion droplets, and less in the aqueous phase. The fact that quaternary ammonium compounds may be present in the aqueous phase in a very small amount only, or not present, leads to a loss of preservative effect or poor preservative effect, as well as to less toxic emulsions.

Thus, one of the goals of this invention is to provide stable cationic emulsions comprising a reduced amount of benzalkonium chlorides, and still using said benzalkonium chlorides as a source, or the only source, of cationic agents, said emulsions being preserved or not.

Another goal of the present invention is to provide emulsions that are not toxic, even if they comprise quaternary ammonium compounds.

Preferably, the emulsions of the invention are useful for ophthalmic purposes.

In the meaning of this invention,

"Cationic emulsions" are emulsions having a positive zeta potential, preferably a zeta potential higher to 10 mV;

"alkyl" means a saturated or unsaturated hydrocarbon chain;

"long alkyl chain" are alkyl moieties having at least 12 carbon atoms;

"quaternary ammonium compounds" refer to ammonium halides in which the nitrogen atom is substituted by only one or at least one alkyl group having at least 12 carbon atoms;

quaternary ammonium compounds also, but not exclusively, include n-alkyl dimethyl benzyl ammonium chloride also called benzalkonium chloride (hereinafter also referred to as BAK or ADBAC); n-alkyl dimethyl benzyl ammonium bromide; n-alkyl trimethyl ammonium bromide (also referred to as ATAB), n-alkyl meaning an alkyl group of at least 12 carbon atoms;

"C14-alkyl ammonium halides" means ammonium halides in which the nitrogen atom of the ammonium group is substituted by at least one alkyl group having at least 14 carbon atoms.

"BAK C12" refers to benzododecinium chloride (CAS 139-07-1);

"BAK C14" refers to myristalkonium chloride (CAS 139-08-2);

"BAK C16" refers to cetalkonium chloride or CKC (CAS 122-18-9);

"ATAB C12" refers to lauryl trimethyl ammonium bromide (CAS 1119-94-4); "ATAB C14" refers to Myristil trimethyl ammonium bromide (CAS 1119-97-7); "ATAB C16" or "CTAB" refers to Cetyl trimethyl ammonium bromide (CAS 57-09-0), "MCT" means Medium chain triglycerides; for the experimentation, Mygliol 812 (Sasol, Germany) was the MCT used;

"ND" means "not determined".

The invention relates to a cationic oil-in-water emulsion comprising an ammonium halide composition as cationic agent. The ammonium halide composition includes in a preferred embodiment only one ammonium halide, which is C16-alkyl quaternary ammonium halide.

The oil-in-water emulsion of the invention presents the advantages to be very stable and non toxic, compared to emulsions comprising benzalkonium chlorides.

By cationic oil-in water emulsion is understood an oil-in-water emulsion having a positive zeta potential. The emulsion of the invention has a positive zeta potential and is stable, which means that it keeps a positive zeta potential overtime.

In a preferred embodiment, the oil-in-water emulsion according to the invention includes droplets of size 100 to 500 nm, preferably 200 to 300 nm.

In a preferred embodiment, the oil-in-water emulsion of the invention is useful for eye care or for the treatment of eye diseases or eye conditions.

In a preferred embodiment of the present invention, eye diseases or eye conditions means a dry eye condition.

A diminution of the quantity of tears produced and distributed through the lachrymal ducts or a decrease in the stability of the tear film produced, results in a condition of the eye referred to as dry eye. Dry eye conditions act to decrease visual acuity, produce discomfort, ranging from mild to intense and eventually, if allowed to remain untreated and uncorrected, result in permanent damage with degradation of the exposed ocular tissues, with a complete breakdown of corneal tissue necessitating, in the extreme, corneal transplants.

The symptoms associated with dry eye are often exacerbated with subjects using contact lens.

A dry eye condition in this context therefore refers to dry eye accompanying lacrimal fluid reduction, tear deficiency, xerosis of the eye, Sjogren's syndrome, keratoconjunctivitis sicca (KCS), atopic keratoconjunctivitis sicca (AKC), vernal keratoconjunctivitis (VKC), Stevens-Johnson syndrome, pemphigoid of the eye, marginal blepharitis, failure in eyelids closure, or sensory nerve numbness, dry eye accompanying allergic conjunctivitis, dry eye after viral conjunctivitis, dry eye after cornea surgery including laser in situ keratomileusis (LASIK), dry eye after cataract surgery, dry eye associated with contact lens wearing, or dry eye associated with VDT tasks More preferably, the oil-in-water emulsion according to the invention comprises:
a) an oil phase,
b) 0.0005% to 0.1% w/w preferably 0.001 to 0.02% w/w of the weight of the emulsion of a composition of ammonium halides according to the invention, as described hereabove, to the weight of the emulsion
c) surfactants,
d) optionally antioxidants, tonicity, viscosifying, pH adjusting, buffering, preservative, solubilizers, chelating or thickener agents,
e) water.

In an embodiment of the present invention, said composition of ammonium halides comprises at least one ammonium quaternary ammonium halide, in which the nitrogen atom of the ammonium group is substituted by only one or at least one alkyl group having at least 12 carbon atoms, said composition including:
at least 20% in weight by weight of the total composition of ammonium halides in which the nitrogen atom is substituted by only one or at least one alkyl group having at least 14 carbon atoms, preferably 14 or 16 carbon atoms and
more than 5%, preferably more than 7% in weight by weight of the total composition, of ammonium halides in which the nitrogen atom is substituted by only one or at least one alkyl group having at least 16 carbon atoms.

According to a preferred embodiment of this invention, the composition of ammonium halides comprises only C16-alkyl quaternary ammonium halide, more preferably ammonium chloride or bromide, in which the nitrogen atom of the ammonium group is substituted by only one or at least one alkyl group having 16 carbon atoms.

Preferably, the composition of ammonium halides comprises C16-alkylbenzyl ammonium halide, preferably C16-alkylbenzyldimethyl ammonium halide, preferably BAK C16.

According to an embodiment of the present invention, the composition of ammonium halides comprises a C16-alkyl quaternary ammonium halide, in which the nitrogen atom of the ammonium group is substituted by two or three lower alkyl groups, preferably by two or three methyl groups.

Thus, in a preferred embodiment of the present invention, said oil-in-water emulsion comprises 0.0005 to 0.1% of C16-alkyl quaternary ammonium halide, in weight by weight of the emulsion.

According to a preferred embodiment, the emulsion of the invention comprises an oil phase, comprising mineral oil, castor oil, MCT, corn oil, olive oil, soybean oil or any suitable vegetable oil, preferably said oil phase comprises mineral oil, castor oil or MCT.

According to a preferred embodiment, the emulsion of the invention further comprises tyloxapol.

According to a preferred embodiment, the emulsion of the invention further comprises a tonicity agent such as for example glycerol, mannitol, sorbitol, sodium chloride; others surfactants such as poloxamer; and optionally at least one buffering agent such as for example citrate, phosphate, tris, borate, acetate, carbonate, borate-polyol complexes, histidine, gluconate and lactate.

In one preferred embodiment of the present invention, said emulsion comprises mannitol as tonicity agent.

In another preferred embodiment of the present invention, said emulsion comprises glycerol as tonicity agent.

Preferably, the emulsion includes 1 to 5% of oil phase, preferably of MCT castor oil or mineral oil, in weight by weight of the emulsion.

Preferably, the mineral oil phase is a mixture of heavy and light mineral oil.

The main droplet core is composed by 50% light mineral oil and 50% heavy mineral oil.

Mineral oil is a mixture of refined liquid saturated aliphatic (C14-C18) and cyclic hydrocarbons obtained from petroleum. Light mineral oil is less viscous and has a lower specific gravity than heavy mineral oil. Heavy and light mineral oil are well known excipients, used in a variety of pharmaceutical formulations including oral, and topical (up to 95%) preparations. In ophthalmic ointments, mineral oil can be found as an excipient at concentrations of up to 60% A combination of light and heavy mineral oil in ophthalmology has been recognized by the US authorities as bearing emollient properties particularly adapted to dry eye treatment (21 CFR 349).

Preferably, the emulsion includes 0.1 to 1% of surfactants, such as tyloxapol and optionally poloxamer 188 and/or polysorbate 80 and/or tocopherol polyethylene glycol succinate and/or sorbitan monolaurate, in weight by weight of the emulsion.

Preferably, the emulsion comprises 0.3% of tyloxapol and optionally 0.1% of poloxamer 188, in weight by weight of the emulsion.

Preferably, the emulsion comprises 0.1% to 5% of tonicity agent(s), more preferably 0.5% to 4% and even more preferably 0.9% to 3.3%, in weight by weight of the emulsion.

In one embodiment, the emulsion comprises 0.1% to 5% of mannitol, more preferably 0.5% to 4% and even more preferably 0.9% to 3.3%, in weight by weight of the emulsion.

In another embodiment, the emulsion comprises 0.1% to 2.5% of glycerol, more preferably 0.19% to 1.6%, in weight by weight of the emulsion.

In one preferred embodiment of the present invention, the emulsion comprises light and heavy mineral oil, tyloxapol, poloxamer 188, mannitol and cetalkonium chloride. Preferably, said emulsion comprises 0.5% of light mineral oil, 0.5% of heavy mineral oil, 0.3% of tyloxapol, 0.1% of poloxamer 188, 3.3% of mannitol, and 0.002% of cetalkonium chloride, in weight by weight of the emulsion.

In another preferred embodiment of the present invention, the emulsion comprises light and heavy mineral oil, tyloxapol, poloxamer 188, glycerol and cetalkonium chloride. Preferably, said emulsion comprises 0.5% of light mineral oil, 0.5% of heavy mineral oil, 0.3% of tyloxapol, 0.1% of poloxamer 188, 1.6% of glycerol, and 0.002% of cetalkonium chloride, in weight by weight of the emulsion.

According to a preferred embodiment of the invention, the emulsion is hypotonic with regards to the normal tears tonicity.

According to a preferred embodiment, the oil-in-water emulsion of the invention is less toxic than a solution comprising the same amount of the same C16-alkyl quaternary ammonium halide, in weight by weight of the solution. For example, the toxicity can be evaluated by a redness test or a Draize test as shown in the examples.

According to a preferred embodiment, the oil-in-water emulsion of the invention is less toxic than an emulsion comprising 0.01 to 0.1% of BAK in weight by weight of the emulsion, said BAK being a mixture of C12, C14 and C16-alkyl quaternary ammonium halide complying to US or European Pharmacopeia specifications.

According to a preferred embodiment, the oil-in-water emulsion of the invention does not induce redness in albino rabbit conjunctiva before administration of 9 drops of 50 μl, said drops being administrated each 5 minutes, preferably before administration of 11 drops, and more preferably before administration of 13 drops.

According to a first embodiment, the emulsion does not contain any active principle. In this embodiment, the emulsion is particularly useful as artificial tears, or for the treatment of dry eye condition such as for example Dry Eye Syndrome or Chronic Dry Eye Disease (CDED), both clinically known as keratoconjuctivitis sicca.

According to a second embodiment, the composition of the invention contains an active principle.

In one embodiment, said active principle is selected from secretagogues such as pilocarpine or celameline, immunosuppressive agents such as natural or synthetic cyclosporins, tacrolimus or sirolimus, mucin secretagogues such as 15(S)-HETE, ecabet or diquafosol, androgen mimetics, flaxseed oil supplements, steroids, agonists of adenosine A3 receptor, squalene, vitamin A; said active principle being preferably cyclosporine.

In another embodiment, said active principle is chosen among the active substances capable of having additional or synergistic therapeutic effects for treating KCS.

Preferably, said active principle can be selected in the group comprising astringents such as zinc sulfate, demulcents including cellulose derivatives, carboxymethylcellulose sodium, hydroxyethyl cellulose; hypromellose, methylcellulose, dextran 70, gelatin, polyethylene glycol 300, polyethylene glycol 400, polysorbate 80, propylene glycol, polyvinyl alcohol and povidone such as polyethylene glycol 6000, emollients such as lanolin preparations or oleaginous ingredients, vasoconstrictors such as naphazoline, ephedrine, tetrahydrozoline and phenylephrine salts.

In an embodiment of the invention, the oil-in-water emulsion is preserved.

In another embodiment of the invention, the oil-in-water emulsion is unpreserved; in an embodiment, the emulsion is packaged in unitary doses; in another embodiment, the emulsion is packaged in suitable multidose containers.

The present invention also relates to the oil-in-water emulsion as described here above, having a high viscosity, and being dispensed to the patient in the form of a gel suitable for ophthalmic use.

Another object of the present invention is also a medicament comprising the oil-in-water emulsion as described here above.

The present invention also relates to a kit for dry eye treatment comprising a first emulsion as described here above, which does not comprise an active principle, and a second emulsion which contains an active principle, preferably cyclosporine.

According to an embodiment said second emulsion comprising an active principle is an emulsion according to the present invention.

According to another embodiment, said second emulsion comprising an active principle is any emulsion suitable for ophthalmic use.

Another object of this invention is a pre-concentrate of the therapeutic oil-in-water emulsion of the invention and a process for manufacturing said pre-concentrate.

According to this invention, a pre-concentrate is defined as an emulsion having an amount of oil higher than the amount of oil of the therapeutic emulsion administered to a patient. In a first embodiment, the amount of oil in the pre-concentrate is of at least 4% v/v. In a second embodiment, the amount of oil in the pre-concentrate is of at least 8% v/v. In a third embodiment, the amount of oil in the pre-concentrate is of at least 10% v/v., preferably of at least 20% v/v, more preferably of at least 30% v/v.

The pre-concentrate may be in a liquid form or in a gel form, or in any form suitable in view of its further dilution with water.

According to an embodiment, the pre-concentrate of ophthalmic oil-in-water emulsion according to the present invention may be sterilized, for example, by heat, such as by autoclaving, or by filtering or filtration, or by irradiation, or by gas sterilization. In another embodiment, the concentrate of the ophthalmic emulsion is prepared in an aseptic manner.

This invention also relates to a process for manufacturing a pre-concentrate of a therapeutic oil-in-water emulsion comprising the steps of emulsifying/mixing the oil phase with an aqueous phase and with surface-active components), wherein the optionally active principle is dissolved in the oil phase. The process for manufacturing said pre-concentrate comprises emulsifying an amount of oil with an aqueous phase and with suitable surfactants, in order to obtain an emulsion having an amount in oil higher than the amount in oil of the corresponding emulsion to be administered for therapeutic purposes.

Before beginning the manufacturing process, the therapeutic oil-in-water emulsion is designed, with a wished concentration of oil, the type of oil (suitable for ophthalmic use, such as for example mineral oil, castor oil, or MCT) the type of elements needed for emulsification such as surfactants for example, and optionally an active principle. The concentration of the concentrate is then decided, depending on the industrial volumes needed.

This invention also relates to a process for manufacturing a therapeutic oil-in-water emulsion comprising (1) manufacturing a pre-concentrate of an ophthalmic oil in water emulsion, said pre-concentrate having a content in oil of at least 4% v/v, preferably of 10% v/v or more, more preferably of 20% v/v or more, even more preferably of 30% v/v or more by emulsifying/mixing an oil suitable for ophthalmic use selected in the group comprising mineral oil, castor oil and MCT, said oil phase containing optionally one or more active principle and a C16-alkyl quaternary ammonium halide and with surface-active component(s), with an aqueous phase and then (2) diluting one volume of the resulting pre-concentrate with 2 to 50 volumes of water.

According to an embodiment, the emulsification is such that the droplet size or the distribution of the droplet size in the pre-concentrate is about the same as the droplet size or the distribution of the droplet size of the therapeutic oil-in-water emulsion.

According to an embodiment, the diluting water may comprise additives selected from the group comprising tonicity agents, such as for example NaCl, glycerol or mannitol, viscosifying agents, buffering agents, preservatives, antioxidants or colorants.

According to an embodiment, the diluting water may also comprise a C16-alkyl quaternary ammonium halide.

Then, according to the invention, a pre-concentrate of this desired emulsion is produced by mixing the oil suitable for ophthalmic use, with an aqueous phase and with surface-active component(s); the average hydrophilic-lipophilic balance (HLB) of the surface-active component(s) may advantageously be about equal to the HLB or average HLB emulsion requirement of the oil or oils used in the present compositions.

An advantage of this invention is to produce large volumes of emulsions without having to scale-up the emulsifying process.

This invention relates to a process for manufacturing a therapeutic oil-in-water emulsion according to the invention, comprising manufacturing a concentrate according to the above-mentioned process and then diluting said concentrate, by mixing 1 volume of concentrate with 2 to 50 volumes of water, to obtain a final therapeutic emulsion having an oil content of 5% v/v of less, preferably of 3% v/v or less, more preferably of 2% v/v or less, even more preferably of 1% v/v or less.

This invention also relates to a method for the treatment of ocular diseases or conditions consisting in the administration to a patient of an ophthalmic emulsion prepared from a pre-concentrate, according to the above described process.

The invention also relates to oil-in-water emulsions obtainable by the process of the invention, i.e. by manufacturing a concentrate including optionally an active principle, and then diluting said concentrate with 2 to 50 volumes of water, said water optionally comprising additives, such as for example tonicity agents, viscosifying agents, buffering agents, preservatives, antioxidants or colorants.

One advantage of the invention is that the oil-in-water emulsions obtained by dilution of the concentrates are formed with reduced energy input.

The following examples and figures illustrate the invention and should not be interpreted in any way as reducing the scope of this invention.

FIG. 1 refers to the timing of appearance of redness in ocular surface.

Figure 2:
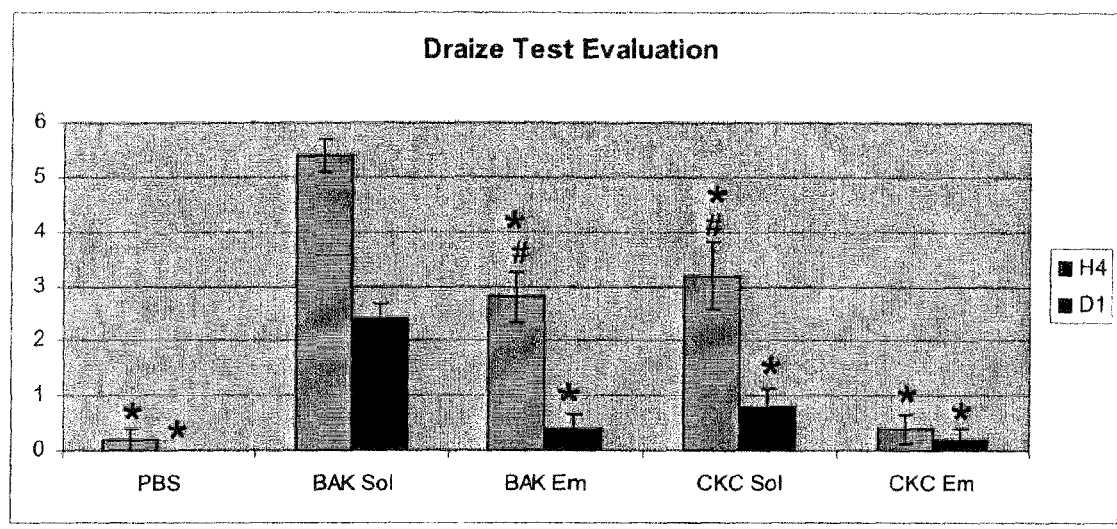

FIG. 2 refers to Draize Test evaluation.

EXAMPLES

All concentrations in the emulsion formulae are expressed in weight/weight of the entire formulation, unless stated differently.

Example 1

Reduced Toxicity of Quaternary Amines when Incorporated Into Emulsions

Materials:
1. Solution at 0.02% BAK (BAK Sol)

| Excipients | Z01SOL472 |
|---|---|
| BAK US | 0.02 |
| NaCl | 0.612 |
| Tris Buffer 5 mM pH 7.1 | 0.069% Tris HCl |
|  | 0.006% Tris Base |
| Water | Ad 100 |

2. Emulsion at 0.02% BAK (BAK Em)

| Excipients | Z01EM471 |
|---|---|
| Mineral oil heavy | 0.500 |
| Mineral oil light | 0.500 |
| Tyloxapol | 0.300 |
| BAK US | 0.02 |
| Tris Buffer 5 mM pH 7.1 | 0.069% Tris HCl |
|  | 0.006% Tris Base |
| Poloxamer 188 | 0.100 |
| Glycerol | 1.6 |
| Water (up to 100) | Ad 100 |

3. Solution at 0.002% CKC (CKC Sol)

|  | Z01SOL473 |
|---|---|
| CKC | 0.002 |
| NaCl | 0.626 |
| Tris Buffer 5 mM pH 7.1 | 0.069% Tris HCl |
|  | 0.006% Tris base |
| Water | Ad 100 |

4. Emulsion at 0.002% CKC (CKC Em)

| Excipients | Z01EM264 |
|---|---|
| Mineral oil heavy | 0.500 |
| Mineral oil light | 0.500 |
| Tyloxapol | 0.300 |
| CKC | 0.002 |
| Tris Buffer 5 mM pH 7.1 | 0.069% Tris HCl |
|  | 0.006% Tris Base |
| Poloxamer 188 | 0.100 |
| Glycerol | 1.6 |
| Water (up to 100) | Ad 100 |

5. PBS

Methods:

Albino rabbits were administrated with 1 drop (50 μl) each 5 minutes, for 15 times.

1/ Evaluation of Toxicity by Time of Redness and DRAIZE Test Items Analyzed at H4 and D1.

The time of the beginning of the redness in conjunctiva following the 15 times of instillations was evaluated (FIG. 1). PBS did not induce any redness during all instillation period (data not shown). BAK Sol induced conjunctival redness very fast, about 10 to 15 minutes after the first instillation (after 2-3 drops). BAK Em, CKC Sol-instilled groups showed redness at about 25-35 minutes after the first instillation of eye drops (after 5-7 drops). CKC Em presented a visible redness at almost the end of the experimentation: 60 to 65 minutes after the first instillation (after 12-13 drops).

Draize Test clearly showed that at four hours (H4) after the last instillation the ocular irritation was the most important in BAK Sol-instilled group, which was higher than BAK Em and CKC Sol groups (with no difference between these two groups). BAK Sol, BAK Em, CKC Sol all showed higher ocular irritation than CKC Em, which presented no difference with PBS-instilled group (FIG. 2).

One day after the administrations (D1), PBS, BAK Em, CKC Sol and CKC Em all returned to normal aspect without difference among them. But BAK Sol still induced more important ocular irritation than all other groups (P<0.0001).

Example 2

Stability of the Emulsions of the Invention

1. Emulsions Composition
Some emulsions are described below:

|  | Z01EM206 | Z01EM209 |
|---|---|---|
| MCT | 2% | 2% |
| Tyloxapol | 0.3% | 0.3% |
| BAK C16 (CKC) | 0.02% | 0.025 mM |
| Poloxamer 188 | 0.1% | 0.1% |
| glycerol | 2.25% | 2.25% |
| water | qsp100 | qsp100 |

| Composition | Z01EM419 | Z01EM264 | Z01EM387 | Z01EM418 | Z01EM418 |
|---|---|---|---|---|---|
| Light mineral oil | 0.5% | 0.5% | 0.5% | 0.5% | 0.5% |
| Heavy mineral oil | 0.5% | 0.5% | 0.5% | 0.5% | 0.5% |
| Tyloxapol | 0.3% | 0.3% | 0.3% | 0.3% | 0.3% |
| Poloxamer 188 | 0.1% | 0.1% | — | — | — |
| PG | — | — | 0.19% | — | — |
| PEG 300 | — | — | 0.19% | — | — |
| PEG 400 | — | — | 0.19% | — | — |
| Mannitol | 3.3% | — | 2% | 2.5% | 2.9% |
| Glycerol | — | 1.6% | 0.19% | 0.19% | — |
| Cetalkonium chloride (CKC) | 0.002% | 0.002% | 0.002% | 0.002% | 0.002% |
| Tromethamine | 0.006% | 0.006% | — | — | — |
| Tris HCl | 0.071% | 0.071% | — | — | — |
| Water | Up to 100% | Up to 100% | Up to 100% | Up to 100% | Up to 100% |

| Composition | Z01EM393-4 | Z01EM395-6 |
|---|---|---|
| MCT | 1-2% | 1-2% |
| Tyloxapol | 0.3% | 0.3% |
| PG | 0.4% | — |
| Mannitol | — | 0.9% |
| Glycerol | 1% | 1% |
| Cetalkonium chloride (CKC) | 0.01% | 0.01% |
| Water | Up to 100% | Up to 100% |

2. Emulsions Preparation

The oily and the water phases of the emulsion, which might contain or not an active principle, may be separately heated to an appropriate temperature. This temperature may be the same in both cases. Surfactants might be dissolved in the oil, water phase or in both. A first coarse emulsion is generated by magnetic stirring, and the droplet size is reduced by high shear mixing, high pressure homogenization, or both.

The oil-in-water emulsions of the present invention can be sterilized after preparation using heat, for example, autoclave steam sterilization.

3. Impact of Chain Length on Emulsions Characteristics
a) Emulsion Droplet Size

The mean diameter of the oil droplets is determined by dynamic light scattering using a High Performance Particle Sizer type HPPS 5001 (Malvern Instruments, Worcestershire, UK). Measurements are performed at 25° C. following dilution of the emulsion in double distilled water.

TABLE 1

Emulsions droplet size values (nm)
Emulsions of Table 1 and Table 2 contain 2% MCT, 0.3% Tyloxapol and 0.1% Poloxamer 188 and 2.25% glycerol and compositions of BAK; Concentrations of BAK range from 0.001 to 0.1% in weight to the weight of the emulsion.

|  | 0.001% | 0.0025% | 0.005% | 0.01% | 0.02% | 0.04% | 0.1% |
|---|---|---|---|---|---|---|---|
| BAK C12 | — | — | 198 | 263 | 230 | 225 | 180 |
| BAK C14 | — | 204 | 190 | 190 | 155 | 238 | 185 |

TABLE 1-continued

Emulsions droplet size values (nm)
Emulsions of Table 1 and Table 2 contain 2% MCT, 0.3% Tyloxapol and 0.1% Poloxamer 188 and 2.25% glycerol and compositions of BAK; Concentrations of BAK range from 0.001 to 0.1% in weight to the weight of the emulsion.

|  | 0.001% | 0.0025% | 0.005% | 0.01% | 0.02% | 0.04% | 0.1% |
|---|---|---|---|---|---|---|---|
| BAK C16 | 220 | 210 | 148 | 180 | 155 | 188 | 183 | b) Emulsion Zeta Potential

Zeta potential can be measured by a zetameter such as Zetasizer 2000, Malvern Instruments Ltd, UK. The zeta potential of the emulsion droplet surface is determined by electrophoretic mobility. Measurements are performed at 25° C. following dilution at 1:250 of the emulsion in double distilled water. The electrophoretic mobility is converted into zeta potential values through the Smoluchowsky equation. The following table and graph show the evolution of the zeta potential (indicative of the surface charge) at increasing concentrations of QA. It can be observed that for more lipophilic (longer) chain lengths, positive charges are attained more rapidly and at lower concentrations, suggesting a preferential partition within the oil droplet surface.

TABLE 2

Emulsions zeta potential values (mV)

|  | 0.001% | 0.0025% | 0.005% | 0.01% | 0.02% | 0.04% | 0.1% |
|---|---|---|---|---|---|---|---|
| BAK C12 | — | — | −6.9 | +4.2 | +7.9 | +16.8 | +23.8 |
| BAK C14 | — | +11.4 | +19.6 | +22.9 | +28.4 | +39.3 | +44.5 |
| BAK C16 | +16.2 | +24.4 | +31.4 | +36.7 | +44.1 | +47.2 | +48.9 | c) Emulsion Stability Over Time

The stability of the emulsions can be evaluated by the evolution of their aspect, with a visual score with a visual score going from 13—best aspect to 1—total phase separation.

It can be observed from the following table that, at equimolar concentration, longer (more lipophilic) chain length QA results in more stable emulsion.

| Type and conc. of QA | After preparation (T0) | Following 3 months at 40° C. |
|---|---|---|
| 0.25 mM BAK C12 | 12 | 2 |
| 0.25 mM BAK C14 | 13 | 7 |
| 0.25 mM BAK C16 | 13 | 9 |
| 0.5 mM BAK C12 | 10 | 2 |
| 0.5 mM BAK C14 | 13 | 7 |
| 0.5 mM BAK C16 | 11 | 9 |

The invention claimed is:

1. An oil-in-water emulsion comprising:
   2% w/w of medium chain triglycerides;
   0.005% w/w of cetalkonium chloride;
   0.3% w/w of tyloxapol;
   0.1% w/w of poloxamer 188;
   2.25% w/w of glycerol; and
   cyclosporine.

2. The oil-in-water emulsion according to claim 1, further comprising buffering agents and/or at least one tonicity agent.

3. The oil-in-water emulsion according to claim 2, wherein the tonicity agent is mannitol.

4. The oil-in-water emulsion according to claim 1, said emulsion having a positive zeta potential.

5. The oil-in-water emulsion according to claim 1, said emulsion having a droplet size of 100 to 500 nm.

6. The oil-in-water emulsion according to claim 1, said emulsion being hypotonic, relative to normal tears.

7. The oil-in-water emulsion according to claim 1, wherein said emulsion is in the form of a gel suitable for ophthalmic use.

8. A medicament comprising the oil-in-water emulsion according to claim 1.

9. A method of preparing an ophthalmic composition for dry eye treatment, comprising preparing the emulsion according to claim 1 in a gel form.

* * * * *